United States Patent [19]

Wallroth et al.

[11] Patent Number: 5,144,991

[45] Date of Patent: Sep. 8, 1992

[54] FILLING ARRANGEMENT FOR AN ANESTHETIC VAPORIZER

[75] Inventors: Carl-Friedrich Wallroth, Lübeck; Wolfgang Falb, Krummesse; Karl-Ludwig Gippert, Lübeck; Eric Hecker, Stockeldorf, all of Fed. Rep. of Germany

[73] Assignee: Drägerwerk Aktiengesellschaft, Lübeck, Fed. Rep. of Germany

[21] Appl. No.: 726,050

[22] Filed: Jul. 5, 1991

[30] Foreign Application Priority Data

Jul. 14, 1990 [DE] Fed. Rep. of Germany ....... 4022492

[51] Int. Cl.⁵ .............................................. A61M 16/18
[52] U.S. Cl. ..................... 141/192; 141/18; 141/302; 141/319; 222/54; 222/479
[58] Field of Search ............... 141/18, 21, 83, 192, 141/196, 289, 290, 301, 302, 304–307, 319–322, 44, 45, 59; 137/79, 80; 128/200.14, 203.12; 222/54, 479

[56] References Cited

U.S. PATENT DOCUMENTS

| | | | |
|---|---|---|---|
| 1,295,321 | 2/1919 | Hurlbrink | 222/54 |
| 2,719,533 | 10/1955 | Smith | 137/80 |
| 2,815,035 | 12/1957 | Eskin et al. | 137/80 |
| 3,006,507 | 10/1961 | Bauerlein | 222/54 |
| 3,530,905 | 9/1970 | Drager | 141/18 |
| 3,536,108 | 10/1970 | Schreiber | 141/18 |
| 3,577,739 | 5/1971 | Botkin | 141/45 X |
| 4,230,161 | 10/1980 | Billington et al. | 141/302 |
| 4,328,909 | 5/1982 | Jeans | 222/54 |
| 4,867,212 | 9/1989 | Mohr et al. | 141/290 |
| 4,967,932 | 11/1990 | Wiley et al. | 222/54 X |
| 5,038,838 | 8/1991 | Bergamini et al. | 141/59 |

FOREIGN PATENT DOCUMENTS

| | | | |
|---|---|---|---|
| 0190080 | 8/1986 | European Pat. Off. | 128/200.14 |
| 1657174 | 8/1971 | Fed. Rep. of Germany . | |
| 2189472 | 10/1987 | United Kingdom | 141/290 |
| 2217610 | 1/1989 | United Kingdom | 128/203.12 |

OTHER PUBLICATIONS

"Operating Manual 5327.09e", third edition, Dec. 1984, published by Drägerwerk AG of Lübeck, Federal Republic of Germany.

Primary Examiner—Henry J. Recla
Assistant Examiner—Casey Jacyna
Attorney, Agent, or Firm—Walter Ottesen

[57] ABSTRACT

The invention is directed to a filling arrangement for filling and emptying an anesthetic vaporizer with an anesthetic liquid from a supply vessel via a filling channel and a venting channel. The filling arrangement includes a connecting piece for connecting the arrangement to the anesthetic vaporizer and has a blocking device mounted in a conduit member which includes the filling channel and venting channel. The filling arrangement is improved so that it can be reliably handled with anesthetic liquids having a low boiling point. For this purpose, the blocking device includes a temperature-sensitive switching member which enables the filling channel to be opened below a preselected limit temperature and to be closed above this preselected temperature. The preselected temperature is below the boiling point of the anesthetic liquid.

6 Claims, 3 Drawing Sheets

FILLING ARRANGEMENT FOR AN ANESTHETIC VAPORIZER

FIELD OF THE INVENTION

The invention relates to a filling arrangement for filling and emptying an anesthetic vaporizer with an anesthetic liquid from a supply vessel by means of a filling channel. The filling arrangement includes a venting channel and a connecting piece to the anesthetic vaporizer and has a blocking device which is mounted in the conduit assembly of the filling channel and venting channel.

BACKGROUND OF THE INVENTION

A filling arrangement for filling and emptying an anesthetic vaporizer with anesthetic liquid via a supply vessel connected thereto is known from U.S. Pat. No. 4,867,212. The filling arrangement includes a movable tubular conducting member which at one end is connected to the supply vessel and, at the other end, the conducting member has an index connecting piece for connecting into the anesthetic vaporizer. The tubular conducting member has a ventilating channel separate from the filling channel. Both channels extend from the supply vessel to the connecting piece as coaxial lines.

For filling, the connecting piece of the tubular conduit unit is engaged with the anesthetic vaporizer and the supply vessel is lifted. After a switch-over valve on the anesthetic vaporizer has been actuated, the anesthetic liquid flows through the filling channel into the tank of the anesthetic vaporizer because of the hydrostatic pressure, while at the same time, the gas volume displaced from the tank of the anesthetic vaporizer reaches the supply vessel via the venting channel. The filling channel and venting channel have the function of communicating tubes between the supply vessel and the tank of the anesthetic vaporizer.

After ending the filling operation, the supply vessel is lowered and the switch-over valve on the anesthetic vaporizer is again closed. A rotatable joint is provided within the conduit assembly of the tubular conduit piece for lifting and lowering the supply vessel. The supply vessel is pivoted about the rotatable joint. A blocking device is integrated into the rotatable joint which closes the filling channel and the venting channel when the supply vessel is lowered after filling.

The known arrangement has the disadvantage that the blocking device is actuated by the lifting and lowering of the supply vessel independently of what vapor pressure has formed within the supply vessel by the anesthetic liquid. If the supply vessel contains an anesthetic liquid which boils at a low temperature, then it can be impossible to fill the anesthetic vaporizer even at usual room temperatures because of bubble formation. Furthermore, if the blocking device is inadvertently opened such as by rotating the tubular conduit unit, the vaporous part of the anesthetic liquid disposed in the supply vessel can escape to the ambient and the anesthetic liquid begins to boil because of the drop in pressure. After a short time, the entire supply of anesthetic liquid can be vaporized.

German patent publication DE-AS 1,657,174 (U.S. patent application Ser. No. 616,961, filed Feb. 17, 1967) discloses a further filling arrangement for connecting a supply vessel to an anesthetic vaporizer. A coupling system with valves is provided at the connecting location between the anesthetic vaporizer and the supply vessel. The valves are opened by means of coupling pins during the coupling operation. When filling, the anesthetic liquid flows under the force of gravity through a filling channel into the tank of the anesthetic vaporizer and the base chamber of the supply vessel turned upside down is ventilated via a ventilating channel.

It is disadvantageous in this arrangement that the filling operation is affected by anesthetic liquids having a low boiling point since the switching of the filling operation is influenced only by the correct alignment of corresponding coupling pins but is not influenced by the temperature of the anesthetic liquid.

SUMMARY OF THE INVENTION

It is an object of the invention to provide a filling arrangement which is improved in that a reliable manipulation is possible for low boiling anesthetic liquids.

The arrangement of the invention is for filling and emptying an anesthetic vaporizer and has an inlet means for supplying anesthetic liquid and venting gas to and from the vaporizer, the anesthetic liquid having a boiling point and being held in a supply vessel. The arrangement includes: a conduit member having first and second end portions and including structure defining a filling channel and a venting channel separate from the filling channel; an interface piece at the first end for interfacing with the inlet means to removably connect the arrangement to the vaporizer; vessel connecting means provided on the second end portion for detachably connecting the supply vessel to the conduit member; a blocking device mounted in the conduit and including: switching means for switching between an open position wherein the filling channel is open to the vessel and a close position wherein the filling channel is closed to the vessel; and, temperature-sensitive actuation means for actuating the switching means into the open position when the temperature of the anesthetic liquid is below a preselected limit temperature and into the close position when the temperature of the anesthetic liquid is above the preselected temperature; and, the preselected temperature being below the boiling point of the anesthetic liquid.

The advantage of the invention is seen essentially in that the blocking device is provided with a temperature-sensitive switching member by means of which the filling channel only opens below a preselected limit temperature and the anesthetic liquid only then flows from a supply vessel turned upside down into the tank of the anesthetic vaporizer under the action of gravity. Above the limit temperature, the blocking device is brought into its close position by the switching member and the anesthetic liquid flow is interrupted.

In advance of filling, the filling arrangement and the supply vessel must be cooled down to a value below the limit temperature. This can take place in that the filling arrangement and the supply vessel are stored in a refrigerator and are only removed therefrom shortly before filling. For monitoring the limit temperature, the supply vessel can be provided with a temperature indicator which indicates that the temperature is below the limit temperature. The blocking device in the filling channel can be configured as a stroke valve having an axially movable closure part on a valve seat with the closure part being actuated by the switching member.

Alternate blocking devices include sliders which slide along the seat when opening and closing. Other possible alternatives include valves having a rotatable body defining valve faces or membrane blocking valves.

In a preferred embodiment of the invention, the blocking device is configured as a filling valve in the filling channel and a venting valve in the venting channel which together can be actuated by the temperature-sensitive switching member. It is possible to completely block the supply vessel with a blocking device disposed in the filling channel as well as in the venting channel when the limit temperature has been exceeded. The supply vessel can in this way be stored at temperatures above the limit temperature without a separate vessel closure without the vaporous anesthetic liquid escaping to the ambient.

It is advantageous to arrange the blocking device within the supply vessel since the temperature-sensitive switching member is there in direct thermal contact with the anesthetic liquid. If the supply vessel is additionally mounted in an insulating body, then a direct contact with the liquid phase and also the gaseous phase of the anesthetic liquid is possible without influence from outside. With the blocking device within the supply vessel, a possible escape of gas or liquid is interrupted directly at the supply vessel.

In a further embodiment of the invention, the blocking device is arranged within or in the vicinity of the connecting piece. This configuration affords the advantage that the blocking device is only then in the open position when the region of the connecting piece is at a temperature level below the preselected limit temperature, that is, below the boiling temperature of the anesthetic liquid. With this arrangement, the condition is obtained that the anesthetic liquid must be below the limit temperature also in the region of the connecting piece.

In a further advantageous embodiment of the invention, the temperature-sensitive switching member is in the form of an elastic bellows filled with a fluid which is in thermal contact with the anesthetic liquid. The fluid can be a gas or a liquid with a high coefficient of expansion or can be the anesthetic liquid itself which is present within the bellows as a gaseous and liquid phase. When the boiling point is reached, the vapor pressure increases and the bellows expands. The bellows stroke is so dimensioned that when there is a drop below the limit temperature, the filling valve and the venting valve have an adequate opening cross section for the liquid and gas flows. As an alternate to the elastic bellows, a bimetal element can be used having an expansion characteristic matched to the limit temperature. In an especially cost-effective embodiment, the closure part of the filling valve or venting valve is connected directly to the bimetal element.

An advantageous embodiment provides that the filling valve is configured as a sleeve movable through a stroke and guided in the blocking housing with the sleeve closing the bore of the filling channel. The venting valve includes a valve seat and a closure part having a sealing plate seated therein and being movable through a stroke. The closure part and the sealing plate coact to block the venting channel. The sleeve and the closure part are connected to a pin so that they can be actuated in common with the pin being guided in the compensating housing. The closure part is actuated directly by the bellows.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
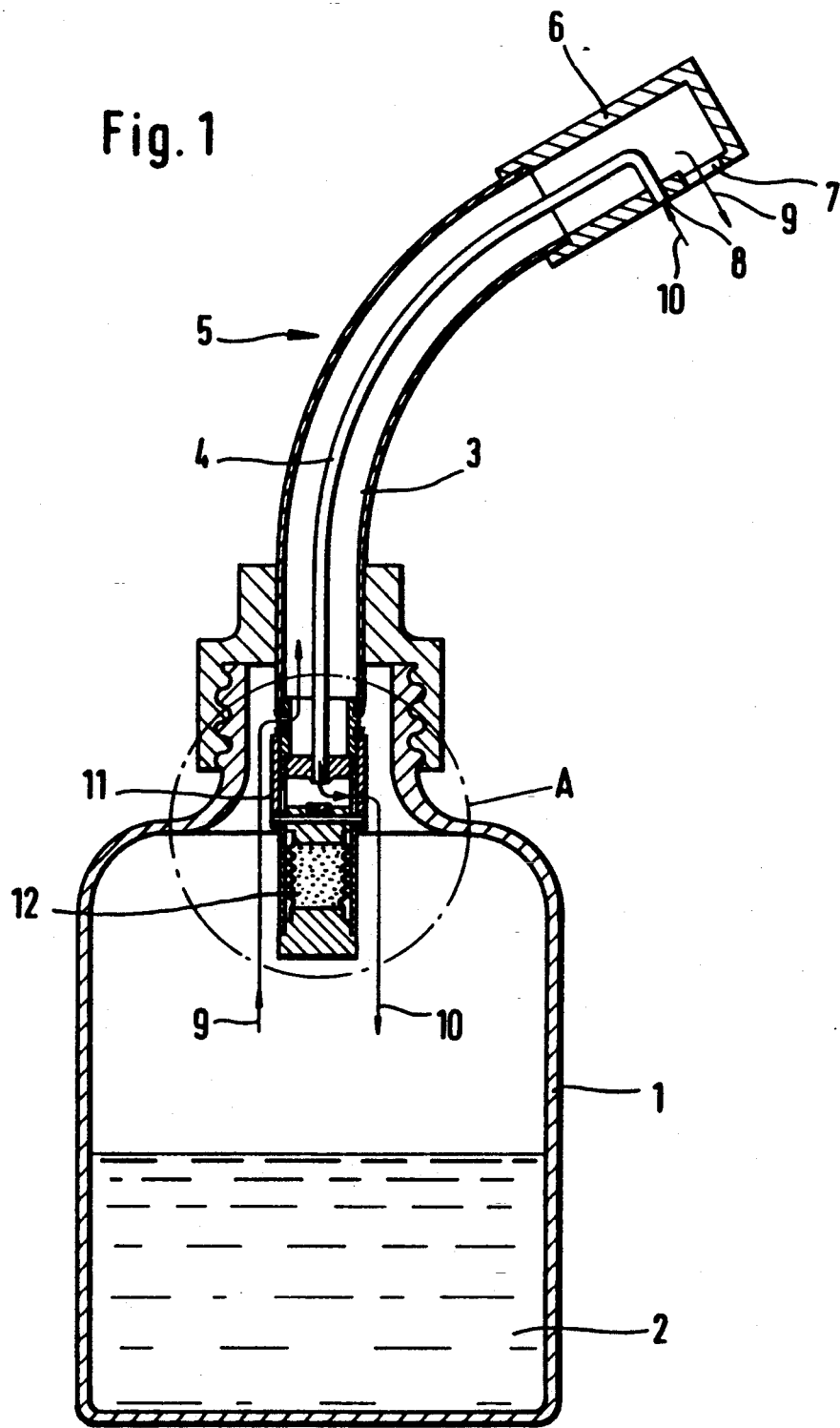
FIG. 1 is a side elevation view, partially in section, showing an embodiment of the filling arrangement according to the invention.

FIG. 1 shows a filling arrangement for filling and emptying an anesthetic vaporizer (not shown). The filling arrangement includes a supply vessel 1 for the anesthetic liquid 2, a filling channel 3 and a venting channel 4. The channels 3 and 4 are configured as a tubular conduit piece 5 and terminate in an index connecting piece 6 which is adapted for insertion into the corresponding index receptacle in the anesthetic vaporizer. The anesthetic liquid flows into or out of the vaporizer through this index receptacle while venting gas also passes through this receptacle between the vaporizer and the supply vessel 1. The procedure for connecting and disconnecting the connecting piece 6 to an anesthetic vaporizer is described in the "Operating Manual 5327.09e", third edition, December 1984, published by Drägerwerk AG of Lübeck, Federal Republic of Germany.

The connecting piece 6 has a filling bore 7 through which the anesthetic fluid flows into the tank of the anesthetic vaporizer and a venting bore 8 through which the supply vessel 1 is vented. The arrow 9 indicates the flow path for the anesthetic liquid 2 while the arrow 10 indicates the gas path for venting.

For filling, the supply vessel 1 is turned upside down so that the anesthetic liquid flows to the throat of the supply vessel 1 and in the direction of arrow 9 into the anesthetic vaporizer. A switch-over valve (not shown) on the anesthetic vaporizer prevents anesthetic liquid 2 from reaching the venting channel 4 before the filling operation is started in that the venting bore is closed.

After the filling channel 3 is filled with anesthetic liquid 2, the filling operation is started in that the venting bore 8 is opened with the switch-over valve and a communicating gas and liquid exchange takes place between the anesthetic vaporizer and the supply vessel 1. After filling, the supply vessel 1 is lowered and the switch-over valve is again closed.

A blocking device 11 and a temperature-sensitive switching member 12 are disposed at the throat of the supply vessel 1. The blocking device 11 and switching member 12 project into the interior of the supply vessel 1 and can be seen in detail "A" shown in FIGS. 2 and 3.

Figure 2:
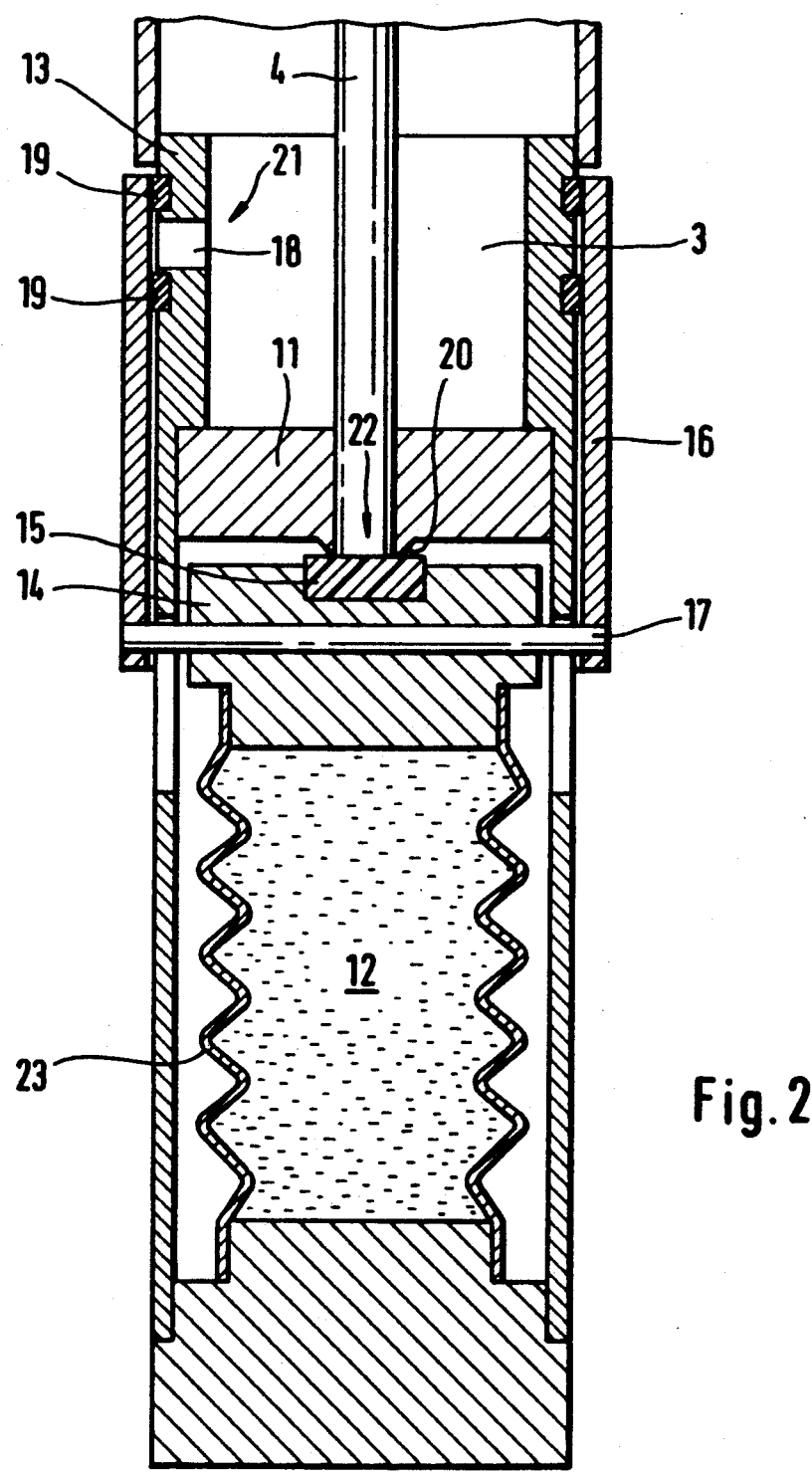
FIG. 2 is an exploded view of detail "A" of FIG. 1 and shows the blocking device in the closed position; and, FIG. 3 corresponds to that of FIG. 2 except with the blocking device in the open position.

FIG. 2 shows the blocking device 11 in the closed position. The filling channel 3 and venting channel 4 open into a blocking housing 13. A temperature-sensitive switching member 12 in the form of an elastic bellows 23 is fixedly mounted in the blocking housing 13. The switching member 12 has a closure part 14 at its free end with a sealing plate 15 mounted in the closure part. The sealing plate 15 lies against the valve seat 20. A sleeve 16 is pushed over the blocking housing 13 and is connected to the closure part 14 via a pin 17 and projects up over a bore 18. Two toroidal sealing rings 19 are provided as seals between sleeve 16 and bore 18.

The filling valve 21 for the filling channel 3 is defined by the sleeve 16 and the bore 18 in the blocking housing 13 and the venting valve 22 is defined by the valve seat 20 and the sealing plate 15. In the position shown in FIG. 2, the filling valve 21 as well as the venting valve 22 are closed. The filling valve 21 and the venting valve 22 conjointly define the blocking device 11.

Figure 3:
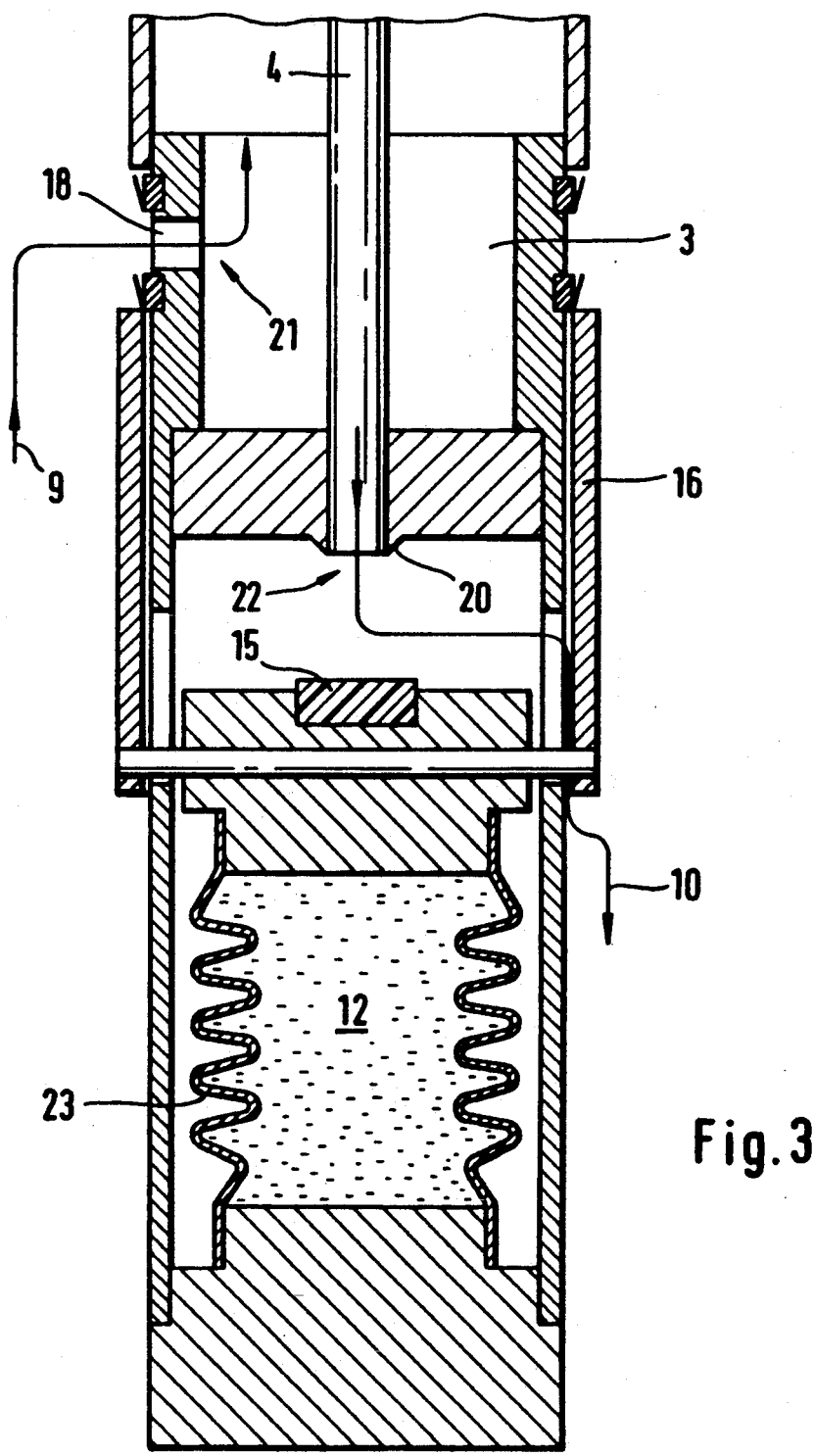

When the ambient temperature has dropped below a limit temperature, the bellows 23 of the switching member 12 shrinks causing the sleeve 16 to clear the bore 18 and to lift the sealing plate 15 from the valve seat 20. This open position of the filling valve 21 and venting valve 22 is shown in FIG. 3. Anesthetic liquid 2 can now flow into the anesthetic vaporizer in the direction of arrow 9 and gas can flow into the supply vessel in the direction of arrow 10. The bellows 23 of the switching member 12 is made of thin sheet brass and filled half way with anesthetic liquid 2. The deformation of the bellows 23 is produced by the vapor pressure which builds up in the interior space of the supply vessel.

It is understood that the foregoing description is that of the preferred embodiments of the invention and that various changes and modifications may be made thereto without departing from the spirit and scope of the invention as defined in the appended claims.

What is claimed is:

1. An arrangement for filling and emptying an anesthetic vaporizer and has an inlet means for supplying anesthetic liquid and venting gas to and from the vaporizer, the anesthetic liquid having a boiling point and being held in a supply vessel, said arrangement comprising:
   a conduit member having first and second end portions and including structure defining a filling channel and a venting channel separate from said filling channel;
   an interface piece at said first end for interfacing with the inlet means to removably connect said arrangement to the vaporizer;
   vessel connecting means provided on said second end portion for detachably connecting the supply vessel to said conduit member;
   a blocking device mounted in said conduit and including: switching means for switching between an open position wherein said filling channel is open to the vessel and a close position wherein said filling channel is closed to the vessel; and, temperature-sensitive actuation means for actuating said switching means into said open position when the temperature of the anesthetic liquid is below a preselected limit temperature and into said close position when the temperature of the anesthetic liquid is above said preselected temperature; and,
   said preselected temperature being below the boiling point of the anesthetic liquid.

2. The arrangement of claim 1, said switching means including first valve means for opening and closing said filling channel with respect to the supply vessel; second valve means for opening and closing said venting channel with respect to the supply vessel; and,
   said actuator means being operatively connected to said first and second valve means for actuating said first and second valve means to open and close said filling and venting channels, respectively.

3. The arrangement of claim 2, said blocking device being mounted at said second end portion of said conduit member so as to be disposed within the supply vessel when the supply vessel is connected to said vessel connecting means;
   said blocking device including a housing mounted in said conduit member;
   said first valve means including bore means formed in said housing for interconnecting said first channel and the interior of the supply vessel; and, a sleeve slideably mounted on said housing for moving between a first position wherein said bore means is clear to permit anesthetic liquid to flow therethrough and a second position wherein said sleeve is over said bore means and the flow of anesthetic liquid is blocked;
   said second valve means including: valve seat means formed in said second channel for interconnecting said second channel with the interior of the supply vessel; and, a closure piece movably mounted in said housing for moving between a first position wherein said valve seat is clear to permit the vessel to be vented and a second position wherein said closure piece closes said valve seat to block the venting of the vessel; and,
   said actuating means including: force transmitting means for transmitting a force in common to said sleeve and said closure part; and, a bellows connected between said force transmitting means and said housing for imparting said force to cause said sleeve and said closure piece to move between said first and second positions.

4. The arrangement of claim 1, said clocking device being mounted at said second end portion so as to be disposed within the supply vessel.

5. The arrangement of claim 1, said blocking device being mounted in said connecting piece.

6. The arrangement of claim 1, said actuating means being an elastic bellows at least partially filled with a fluid; and, said elastic bellows being in thermal contact with the anesthetic liquid.

* * * * *

UNITED STATES PATENT AND TRADEMARK OFFICE
CERTIFICATE OF CORRECTION

PATENT NO. : 5,144,991

DATED : September 8, 1992

INVENTOR(S) : Carl-Friedrich Wallroth, Wolfgang Falb, Karl-Ludwig Gippert and Eric Hecker It is certified that error appears in the above-identified patent and that said Letters Patent is hereby corrected as shown below:

In column 5, line 31:  delete "and".

In column 6, line 46:  delete "clocking" and substitute -- blocking -- therefor.

Signed and Sealed this

Fifth Day of October, 1993

Attest:

BRUCE LEHMAN

Attesting Officer

Commissioner of Patents and Trademarks